(12) United States Patent
Capuano et al.

(10) Patent No.: US 7,912,554 B2
(45) Date of Patent: Mar. 22, 2011

(54) METHOD FOR TREATMENT OF ANEURYSMS

(75) Inventors: Leonilda Capuano, Pointe-Claire (CA); Daniel Nahon, Ottawa (CA); Michael Urick, Chaska, MN (US); Willard W. Hennemann, Québec (CA); Patrick Chauvet, Montréal (CA); Claudia Lückge, Ile Perrot (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 1605 days.

(21) Appl. No.: 11/119,368

(22) Filed: Apr. 29, 2005

(65) Prior Publication Data
US 2005/0222649 A1  Oct. 6, 2005

Related U.S. Application Data

(63) Continuation-in-part of application No. 10/839,766, filed on May 5, 2004, now abandoned, which is a continuation-in-part of application No. 09/964,264, filed on Sep. 26, 2001, now Pat. No. 6,736,809.

(51) Int. Cl.
*A61F 2/00* (2006.01)
(52) U.S. Cl. .......................... 607/101; 607/99; 607/113
(58) Field of Classification Search ............... 606/32, 606/33, 200, 213, 13–15, 27–29; 607/99, 607/101, 113, 88–94; 604/52–53
See application file for complete search history.

(56) References Cited

U.S. PATENT DOCUMENTS

| 5,108,407 | A | * | 4/1992 | Geremia et al. ............. 606/108 |
| 5,222,938 | A | | 6/1993 | Behl |
| 5,275,597 | A | * | 1/1994 | Higgins et al. ................ 606/33 |
| 5,281,215 | A | | 1/1994 | Milder |
| 5,370,608 | A | * | 12/1994 | Sahota et al. ................ 604/20 |
| 5,417,653 | A | | 5/1995 | Sahota et al. |
| 5,423,807 | A | | 6/1995 | Milder |
| 5,749,894 | A | * | 5/1998 | Engelson .................... 606/213 |
| 5,817,144 | A | * | 10/1998 | Gregory ....................... 607/89 |
| 5,868,735 | A | | 2/1999 | Lafontaine |
| 5,885,238 | A | | 3/1999 | Stevens et al. |

(Continued)

OTHER PUBLICATIONS

Fasano, V.A., The Treatment of Vascular Malformation of the Brain with Laser Source, *Lasers in Surgery and Medicine*, vol. 1, pp. 347-356, (1981).

(Continued)

*Primary Examiner* — Roy D Gibson
(74) *Attorney, Agent, or Firm* — Christopher & Weisberg, P.A.

(57) ABSTRACT

A method is disclosed for treating an aneurysm or vascular defect by cooling a target tissue region of the aneurysm or vascular defect to a temperature below body temperature for a preselected time period. The method entails thickening, strengthening, or increasing the density of a blood vessel wall by cooling the blood vessel wall with a cryogenically cooled device. The method also includes irradiating the inner wall of a blood vessel around an aneurysm or vascular defect with various forms of energy to delay or halt aneurysm or vascular defect formation. An energy-emitting element is disposed on the distal end portion of a catheter device to be disposed proximate the aneurysm. Various forms of energy, including visible light energy, laser light energy, ultrasound, microwave and radiofrequency sources may be used to irradiate and treat the aneurysm. In addition, the method may include irradiating a tissue site concomitantly with other treatments, including the delivery of vaso-occlusive compounds, mechanical intravascular devices, or an endovascular graft to the target tissue region.

10 Claims, 6 Drawing Sheets

U.S. PATENT DOCUMENTS

| | | | |
|---|---|---|---|
| 5,902,299 A | | 5/1999 | Jayaraman |
| 5,921,954 A | * | 7/1999 | Mohr et al. ............... 604/508 |
| 5,971,979 A | | 10/1999 | Joye et al. |
| 6,006,755 A | * | 12/1999 | Edwards ............... 128/898 |
| 6,012,457 A | | 1/2000 | Lesh |
| 6,024,740 A | | 2/2000 | Lesh et al. |
| 6,036,697 A | | 3/2000 | DiCaprio |
| 6,051,019 A | | 4/2000 | Dobak, III |
| 6,126,684 A | | 10/2000 | Gobin et al. |
| 6,129,705 A | * | 10/2000 | Grantz ............... 604/103.02 |
| 6,228,109 B1 | * | 5/2001 | Tu et al. ............... 607/113 |
| 6,241,718 B1 | | 6/2001 | Arless et al. |
| 6,375,668 B1 | * | 4/2002 | Gifford et al. ............... 606/200 |
| 6,386,202 B1 | | 5/2002 | Frazee |
| 6,428,563 B1 | | 8/2002 | Keller |
| 6,468,297 B1 | | 10/2002 | Williams et al. |
| 6,532,387 B1 | * | 3/2003 | Marchitto et al. ............... 604/21 |
| 6,576,000 B2 | * | 6/2003 | Carrison ............... 607/92 |
| 6,585,689 B1 | | 7/2003 | Macoviak et al. |
| 2001/0032004 A1 | | 10/2001 | Werneth |
| 2002/0032430 A1 | | 3/2002 | Luo et al. |
| 2002/0065542 A1 | * | 5/2002 | Lax et al. ............... 607/99 |
| 2002/0161351 A1 | | 10/2002 | Samson et al. |

OTHER PUBLICATIONS

Patil, A.A., Electromagnetic Field Focusing (EFF) Probe in Aneurysm Thrombosis, *Acta Neurochirurgica*, vol. 81, pp. 68-71, (1986).

Yamanashi, W.S., et al., Electromagnetically Induced Focused Heat in the Treatment of Surgically Created Aneurysm Models, *Investigative Radiology*, vol. 22, pp. 574-580, (1987).

Yamanashi, W.S., et al., Precision Surgery with an Electromagnetically Induced Current Convergence Probe Application in Aneurysm Treatment, Angioplasty, and Brain Tumor Resection in in Vivo and in Vitro Models, *Medical Instrumentation*, vol. 22, No. 4, pp. 205-216, (1988).

Sieunairine, K., et al., Full-Thickness Burn and Venous Thrombosis Following Intravenous Infuson of Microwave-Heated Crystalloid Fluids, *Burns*, vol. 22, No. 7, pp. 568-569, (1996).

Oskoui, I.S., et al., A Preliminary Study of Laser Tissue Soldering as Arterial Wall Reinforcement in an Acute Experimental Aneurysm Model, Lasers in Surgery and Medicine, *Lasers in Surgery and Medicine*, vol. 32 (5), pp. 346-348, (2003).

J. Raymond, et al., Role of the Endothelial Lining in Persistence of Residual Lesions and Growth of Recurrences After Endovascular Treatment of Experimental Aneurysms, in *Stroke* at 850, (American Heart Association, 2002).

J. Raymond, et al., Long Term Angiographic Recurrences After Selective Endovascular Treatment of Aneurysms with Detachable Coils, in *Stroke* at 1398, (American Heart Association, 2003).

J. Raymond, et al., Beta Radiation and Inhibition of Recanalization After Coil Embolization of Canine Arteries and Experimental Aneurysms—How Should Radiation Be Delivered?, in *Stroke* at 1262, (American Heart Association, 2003).

J. Raymond, et al., Role of the Endothelial Lining In Recurrences After Coil Emoblization—Prevention of Recanalization by Endothelial Denudation, in *Stroke* at 1471, (American Heart Association, 2004).

* cited by examiner

METHOD FOR TREATMENT OF ANEURYSMS

CROSS-REFERENCE TO RELATED APPLICATION

This application is a continuation-in-part of U.S. patent application Ser. No. 10/839,766, filed May 5, 2004, now abandoned entitled METHOD FOR TREATMENT OF ANEURYSMS, which application is a continuation-in-part of U.S. patent application Ser. No. 09/964,264, filed Sep. 26, 2001, now U.S. Pat. No. 6,736,809 entitled METHOD AND DEVICE FOR TREATMENT OF ANEURYSMS, now allowed.

STATEMENT REGARDING FEDERALLY SPONSORED RESEARCH OR DEVELOPMENT n/a

FIELD OF THE INVENTION

The present invention relates to a method and device for treating vascular defects such as aneurysms, dissections, arterio-venous malformation and vulnerable plaque, and in particular, to a method involving the use of a catheter and thermo-cryogenic, electromagnetic, and ultrasonic energy sources concomitantly with an additional treatment to treat tissue.

BACKGROUND OF THE INVENTION

Aneurysms are distensions formed by the localized dilation of the wall of an artery, a vein, or the heart. An aneurysm balloons due to the pressure of blood flowing through an area weakened due to disease, injury, or congenital defect. A "true" or common aneurysm results from the formation of a sac by the arterial wall, or tunica media, which remains unbroken, and may be associated with atherosclerosis. In a "false" or dissecting aneurysm, usually caused by trauma, a fissure in the wall of a blood vessel allows blood to escape into surrounding tissues and form a clot.

Doctors typically monitor the inflammation and progression of aneurysms using devices known in the art such as MRI and CT scanners and by observation of known patient symptoms. Typically, however, early stage aneurysms do not warrant dangerous surgical procedures, even if minimally invasive, due to the associated morbidity risk. Accordingly, the doctors choose a "wait and see" approach. Because surgery for aneurysms is risky, the surgeon may wait for the aneurysm to expand to a certain size before operating, when the risk of complications exceeds the risk of surgery. Accordingly, it would be desirable to treat aneurysms upon early detection rather than wait until they progress to a stage that requires dangerous, expensive surgery, or become life-threatening conditions.

In addition to aneurysms, certain other vascular defects are of interest, such as a dissection. Vascular dissections are similar to aneurysms in that the vessel wall integrity is compromised. However a dissection consists of a laceration of a portion of the vessel wall. Both dissections and lacerations are associated risks stemming from arterial disease.

Therefore, it would be desirable to have a device, coupled with a minimally invasive method, to retard, arrest and even reverse, the processes that lead to vascular defects such as dissections or aneurysm formation, and arterio-venous malformation or vulnerable plaque.

SUMMARY OF THE INVENTION

A method for treating a vascular defect is disclosed. A catheter having an energy-transfer element is positioned and disposed proximate a target tissue region including the vascular defect. Energy is transferred between the energy-transfer element and the target tissue region. The energy may be emitted as a treatment energy from the energy-transfer element, and further directed to be in part absorbed by the target tissue region. The treatment energy may be any of the following group: visible light energy, laser light energy, ultrasonic periodic mechanical vibrational, or ultrasound, energy, and microwave or radiofrequency electromagnetic energy. Alternatively, the energy-transfer element is a heat-absorbing device, and heat is transferred from the target tissue region to the heat-absorbing device. The heat transfer element can include an expansion chamber, wherein a coolant is injected into the expansion chamber. In addition, the treatment method may include providing energy transfer paired with an additional treatment method, including drug delivery, the use of an implanted medical device, a biological filler material, or an endovascular graft.

In another embodiment, a method is provided for thickening, strengthening, or increasing the density of a blood vessel wall. A catheter is provided having an energy-transfer element. The catheter is positioned such that the energy-transfer element is disposed proximate the blood vessel wall. A flow of treatment energy is transferred between the energy-transfer element and the blood vessel wall.

In yet another embodiment, a method is provided for enhancing collagen production in blood vessels proximate a vascular defect. Collagen inducing growth factors are injected into a target tissue region proximate the vascular defect. A device having a discrete light energy-emitting element is provided. The element is disposed proximate to the target tissue region. The energy-emitting element is directed to emit light energy and to irradiate the target tissue region with said light energy. The collagen inducing growth factors are activated with the light energy.

In still yet another embodiment, a method is provided for cryotreating vulnerable plaque. The method provides for the treatment of plaque formed on an interior lumenal surface of a body or blood lumen. A cooling device is positioned at the interior lumenal surface at a point proximate to a plaque formation. The lumenal surface is cooled at the point proximate to the plaque formation to inhibit the progression of plaque formation in which the lumenal surface is cooled to a temperature of less than about zero degrees Celsius.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

As used herein, a "vascular defect" shall mean an aneurysm, a dissection, or vulnerable plaque as further described and set forth herein. An aneurysm is typically characterized by a localized dilatation in a blood vessel, while a dissection occurs when a defect in the lining of a blood vessel allows an opening or tear to develop in the vessel wall.

Vascular or vulnerable plaque is typically caused by coronary artery disease, and involves the formation of plaque, a combination of cholesterol and cellular waste products that form on the interior wall of an artery. Eventually, the plaque deposit can develop a thin covering called a fibrous cap. With plaque progression, the vessel wall can experience inflammation, leading to the erosion of the fibrous cap. The erosion may cause the plaque cap to crack, allowing the underlying plaque elements to come in contact with the blood stream. Exposure of these elements to the blood stream can cause clot formation, leading to coronary artery occlusion, myocardial ischemia and infarction. This particular type of lipid-rich plaque, having active inflammation and the potential to erode the overlying fibrous cap, which in turn can lead to thrombosis and myocardial infarction is called unstable or vulnerable plaque.

Catheter based devices enable access to the weakened arterial wall around an aneurysm, a dissection or venerable plaque, are minimally invasive, and may be employed for a variety of diagnostic and therapeutic functions. Localized application of cold temperatures to the blood vessel wall may serve to strengthen and thicken the distended and dilated tissue of an aneurysm, and make such tissue layers increasingly dense, as well as inhibit the progression of plaque formation. Accordingly, by applying such cold, or cryotreatment, to the aneurysm, dissection or vulnerable plaque site, the aneurysm, dissection or vulnerable plaque may be effectively treated without major surgery.

Figure 1:
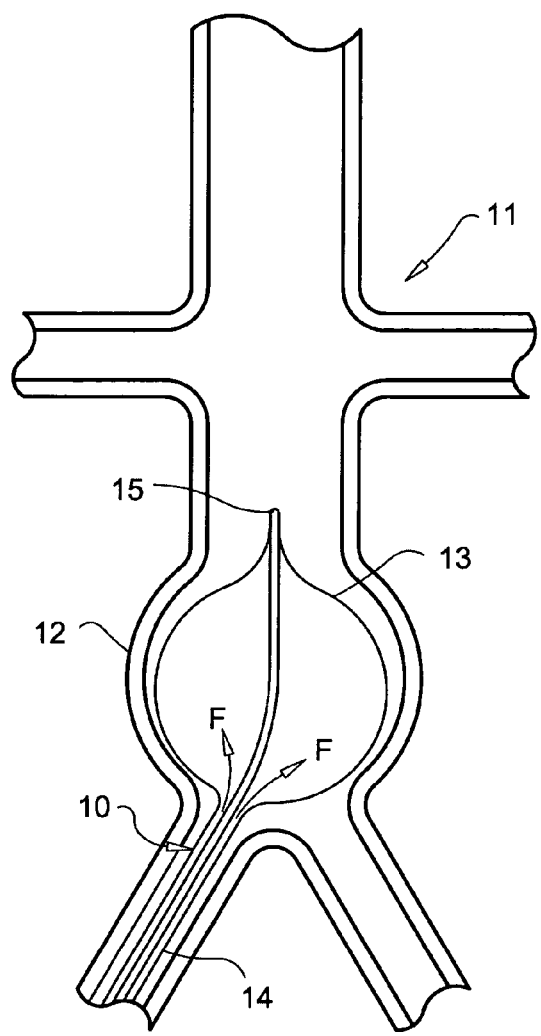
FIG. 1 is a cross-sectional view of a balloon catheter device disposed inside of a blood vessel proximate an aneurysm.

FIG. 1 illustrates a blood vessel and a device during a procedure for cryotreatment of an aneurysm. In FIG. 1, a balloon catheter, labelled generally as 10, is disposed inside of a blood vessel 11 proximate to an aneurysm 12. The balloon catheter 10 includes a flexible, expandable membrane or balloon 13 coupled to a catheter tube 14, wherein the catheter 10 is guided to the desired treatment site via a guidewire 15. In this procedure, the balloon catheter 10 is percutaneously inserted into the vasculature and advanced to the locus of the aneurysm 12. The specific size and shape of the balloon 13 and catheter tube 14 may be determined a priori in order to best fit the targeted artery or blood vessel where an aneurysm has formed. The balloon 13 is thereby inflated to appose the inner walls of the blood vessel proximate the aneurysm 12, so as to enable cryotreatment of the aneurysm 12 tissue.

However, contrary to conventional angioplasty procedures, the dilatation and apposition of the balloon 13 versus the inner walls of the aneurysm is not meant to dilate the blood vessel walls. Rather, the device employed in this procedure uses a balloon-tipped catheter configured to receive the flow of a coolant, or cryogenic fluid, therein. High-pressure coolant fluid is connected to the proximal section of the catheter tube 14, which contains several tubes and lumens (not shown) adapted to contain the flow of coolant therein. The coolant used may be any stable working fluid capable of being compressed to high pressure, pumped though small diameter devices, and expanded to produce endothermic cooling at a desired location. Examples of such coolants are nitrogen, nitrous oxide, or any conventionally used refrigerant. The coolant may be in liquid, gaseous, or mixed phase form. The flow system inside of the catheter may be either closed loop, wherein the injected coolant is returned to the source for recycling and re-entry into the device, or open loop, wherein the coolant is pumped through the device only once, whereupon it exits outside the body and is discarded.

The coolant flows through the catheter tube 14 and is injected, generally along coolant flow lines F, into the balloon 13 at the distal tip of the catheter 10, whereupon the balloon 13 expands as the coolant is both vaporized and expanded inside the balloon. The combined evaporation and expansion of the coolant creates endothermic cooling in the near field of the balloon 13. The process is endothermic in that heat, or thermal energy, is absorbed by the balloon 13, and flow of coolant therein, from the surrounding environment: the aneurysm and targeted tissue of the blood vessel wall which forms the aneurysm. This cooling draws heat from the adjacent aneurysm tissue in the coolant flow inside of balloon 13, thereby cooling the aneurysm tissue to temperatures in the range of +20 to −20 degrees Centigrade.

The particular shape of the expanded balloon 13 may be predetermined by the use of a preformed balloon membrane, a memory retaining material, or other structural attribute wherein the expanded balloon 13 is configured to form a particular shape, yet also remain somewhat conformable. The balloon 13 may also be totally conformable, such that the expanded membrane fits to conform to the particular contours of the blood vessel wall of the aneurysm 12, for optimal contact therewith.

Alternatively, the distal tip of the catheter 10 may also include multiple expandable membranes or chambers (not shown), wherein different injection fluids are pumped into separate chambers within a single membrane, or multiple outer membranes. One injection fluid may be used to expand a first chamber, while another cooling fluid may be used to create endothermic cooling in the same or another chamber, as discussed above.

Any tissue near or adjacent to the balloon and flow of coolant therein may be cooled to temperatures below body temperature. The duration of cooling may vary from 15 seconds to up to 20 minutes, depending on the application, and the particular aneurysm targeted. Part or the entire surface of the balloon may be specially treated or affixed with heat conductive elements to create a pattern of cooling on the tissue surfaces targeted. An example of such an endovascular balloon catheter used to cold treat tissues is disclosed in U.S. Pat. No. 6,283,959 B1, the entirety of which is incorporated herein by reference. The tissue forming the aneurysm 12 is thus cold-treated by the catheter device 10, whereupon the balloon 13 is contracted or evacuated, and withdrawn from the treatment site.

The cryotreatment of aneurysm tissue in the prescribed time and temperature ranges discussed above may, among other effects, stimulate a tissue response which results in myointimal thickening of the blood vessel wall and anvential tissue. This thickening helps to minimize the incidence of aneurysm rupture, which can be fatal. Cryotreatment may also result in reparative regeneration of the endothelium, in addition to accelerated myointimal thickening. These overall effects serve to treat and possibly reverse the formation of an aneurysm, leading to significant therapeutic results.

Aneurysmal enlargement results in part from degradation of the extracellular matrix and other structural elements of the blood vessel wall. This in turn is related to an increased activity of proteolytic enzymes such as collagenase and elastase, resulting in destruction of collagen and elastin forming the blood vessel wall. Macrophages and inflammatory cells may also be sources of enzymes, which have a capacity to degrade all the major connective tissues forming the blood vessel wall, including collagen and elastin, all of which contribute to aneurysms. The application of cold temperatures to such tissues may slow or retard the action of such macrophages, proteolytic enzymes, thus diminishing the destruction of collagen and elastin that is vital to the structural integrity of the blood vessel wall. In such a way, cryotreatment may effectively treat aneurysms.

Furthermore, for large blood vessels such as the aorta, aneurysms also exhibit the synthesis and accumulation of new collagen and elastin in the expanding aorta. However, these newly synthesized proteins often lack the intricate fibrillar structure and mature cross-linking necessary to maintain the normal tensile strength of the cellular matrix of the aortic wall. Cryotreatment of such areas may show the ability to compensate for such an effect, allowing the enlarged aortic wall to retain its normal extra-cellular matrix characteristics. In a similar fashion, the application of the cryotreatment to vulnerable plaque sites reduces the inflammation of the blood vessel while increasing the collagen synthesis, to effectively treat vascular plaque.

In general, the balloon 13 as used for cryotreatment, is an apposition device, and not a dilatation device. Accordingly, the strength of materials forming the balloon 13 itself, as well as the fluid pressures therein, are generally not required to be as high as a conventional blood vessel-dilating angioplasty balloon.

The catheter 10 itself may also be combined with an injection element, wherein a therapeutic drug or medication is infused in the target area around the aneurysm 12 in conjunction with the use of the balloon 13 to effect cryotreatment.

Figure 2:
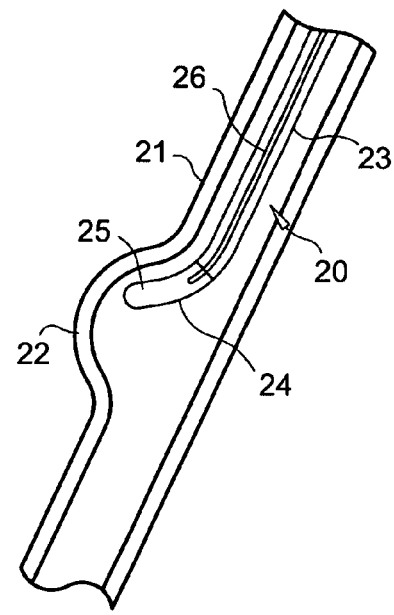
FIG. 2 is a cross-sectional view of a catheter with a cooling segment positioned proximate the arterial wall in an aneurysm.

In another procedure, a fixed diameter catheter device is used, as illustrated in FIG. 2. FIG. 2 shows an endovascular catheter 20 disposed inside of a blood vessel 21 near an aneurysm 22. The catheter 20 includes a catheter tube 23 having a cooling segment 24 disposed at its distal end portion. The catheter 20 may include one or more injection lumens 26, as well as several tubes and lumens (not shown) adapted to contain the flow of coolant therein. Although the distal end of the catheter 20 is shown in a substantially linear or straight configuration, the distal tip can be configured or commanded to assume an annular or helical shape. The catheter 20 is percutaneously inserted into the vasculature and advanced to the aneurysm site 22. A guidewire, rapid-exchange system, or other catheter positioning device may be employed to position the catheter tip at the desired location. Coolant is injected into the catheter 20 via injection lumen 26, and flows through to the distal tip of the catheter, which contains the cooling segment 24. The cooling segment 24 is any heat conductive element, which defines a closed volume expansion chamber 25, wherein coolant may be expanded to low temperatures after it exits the injection lumen 26. The coolant, which may be in mixed liquid or gaseous phase, is injected into the expansion chamber 25, whereby it undergoes both evaporative cooling through a change in phase from liquid to gas, and expansive cooling through a Joule-Thomson throttling process, similar to the those thermodynamic changes discussed with respect to the balloon catheter device 10 of FIG. 1. As with the balloon catheter device 10 embodiment above, these gas-dynamic processes are generally endothermic with respect to the surrounding environment, in that heat is drawn from the tissue forming the surrounding aneurysm 22 so as to cool such tissue to temperatures below normal human body temperature, and indeed below the freezing point of water and beyond. The strength of cooling may be controllably varied by the user by controlling the pressure and flow of coolant in the catheter device. The size and particular shape of the cooling segment 24 may be varied to best fit the contours of the particular aneurysm to be treated, such as a berry aneurysm in the brain, a saccular aortic aneurysm just above the heart, or a fusiform aneurysm in the lower aorta, as is illustrated in FIG. 1.

Figure 3:
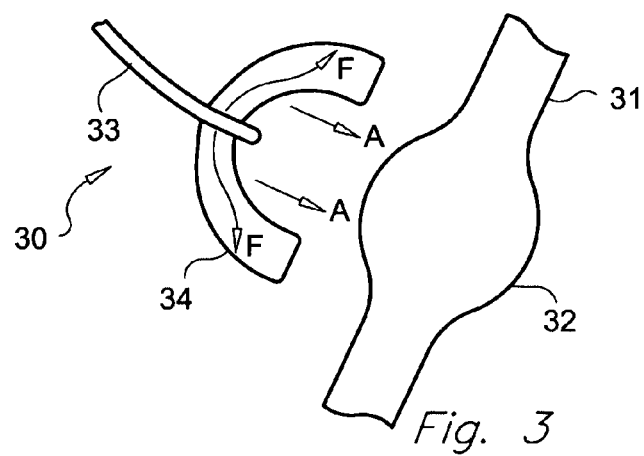
FIG. 3 is a perspective view of a balloon-cuff catheter device for contact with an aneurysm outside the arterial wall.

Although FIGS. 1 and 2 illustrate an approach to treating an aneurysm from within a blood vessel, FIG. 3 shows another embodiment wherein an aneurysm can be approached from the exterior of a blood vessel. In these procedures, the device can be a fixed diameter catheter, a probe, an inflatable device, which is applied to the surface of the aneurysm, or even a fixed, compliant, or inflatable cuff which partially or completely encircles the vessel in the location of the aneurysm, as shown in FIG. 3.

FIG. 3 illustrates a cryotreatment device 30, externally disposed adjacent to or proximate a blood vessel 31 having an aneurysm 32. The device 30 includes a coolant source element 33 having an expandable, inflatable membrane, such as the cuff 34 shown in FIG. 3. The cuff 34 may have a U-shape in order to conformably fit around one hemisphere of a rounded aneurysm 32, as shown in FIG. 3. Alternatively, the cuff 34 may be highly compliant and conformable such that when apposed against an aneurysm of any shape, the outer surface of such cuff 34 conformably rests in contact with such surface and envelops a significant surface area of the aneurysm.

The device 30 includes at least one injection lumen (not shown) in the source element 33 to carry the flow of coolant into the interior of cuff 34. The coolant may then be injected into the cuff 34, such as along the flow lines F shown in FIG. 3. As with the balloon catheter device 10 shown in FIG. 1, the cuff 34 is inflatably expandable by the action of a gas or liquid which may include the coolant or a completely separate source. The cuff 34 may be a preformed balloon membrane, or may include a memory retaining material or other structural attribute wherein the expanded form is configured to form a particular shape, yet also remain somewhat conformable.

Once inflated, the cuff 34 is externally applied in proximity to, or in apposition against, the desired aneurysm treatment site, such as in the direction of arrows A shown in FIG. 3. The flow of coolant in the cuff 34 endothermically cools the target tissue of the aneurysm 32, in accordance with the previous two embodiments of the present invention. The flow of coolant may result in the target tissue being cooled to a temperature between about 0° C. to about −200° C. This approach may be combined with conventional surgery to treat the aneurysm, wherein the cold treatment of the arterial wall is used with other treatment techniques and therapies.

In addition to the methods involving cryogenic thermal cooling, non-thermal energy sources may be used to treat the blood vessel wall proximate an aneurysm, including, among others, visible light energy of a particular wavelength, laser light energy, ultrasound, and microwave and radiofrequency electromagnetic energy. In addition to heat energy transferred by cooling, all such sources of "treatment" energy may have beneficial effects in counteracting the disorders of collagen and elastin synthesis characteristic of aneurysm formation, in addition to being able to create lesions and scar tissue within the walls of blood vessels such as the aorta.

Figure 4:
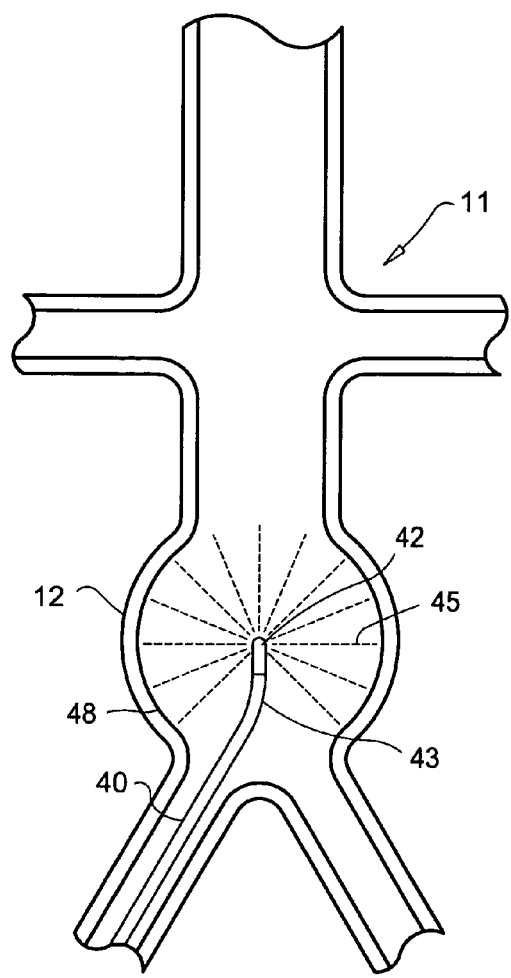
FIG. 4 is a view of a catheter device using photodynamic energy disposed inside of a blood vessel proximate an aneurysm.

FIG. 4 illustrates a catheter 40 disposed inside a blood vessel 11 proximate an aneurysm 12. The catheter 40 includes an energy-transfer device or element 42 disposed at its distal end portion 43. As used herein, an "energy-transfer" device shall mean any device that transfers energy between the device and its environment, wherein energy may flow either to or from the device. In this sense, an energy-transfer device may be either an energy-emitting device or an energy-absorbing device. One example of an energy-absorbing device would be the catheter 10 with balloon 13 in the embodiment shown in FIG. 1, the catheter 20 with cooling segment 24 in the embodiment shown in FIG. 2, or the cryotreatment device 30 with source element 33 and cuff 34 in the embodiment shown in FIG. 3.

In the embodiment illustrated in FIG. 4, the energy-transfer device 42 includes (not shown) a suitable device for emitting energy (labelled in FIG. 4 as dashed lines 45) in the form of waves or particles flowing from the distal end portion 43 of catheter 40 towards the inner wall 48 of the blood vessel 11 proximate the aneurysm 12. Upon contacting the inner wall 48, the cellular structure of the blood vessel 11 absorbs the energy 45, thereby triggering various therapeutic reactions and treating the aneurysm 12.

FIG. 4 illustrates the use of photodynamic visible light energy 45 to treat the aneurysm 12. Such light energy may be anywhere in the visible range, having a wavelength of between 300 to 800 nanometers, or may be tuned to a particular frequency. Photodynamic light energy may be used in conjunction with various collagen inducing growth factors that are either systemically or locally injected into the vasculature and blood stream. When such light energy is thereafter used to irradiate the blood vessel 11 and aneurysm 12, it triggers a reaction in the vasculature with the injected collagen inducing growth factors so as to delay or halt aneurysm formation. Examples of such collagen inducing growth factors are TGF-beta 1, which acts to regulate connective tissue growth factors. The particular wavelength of light, which may be used for such a purpose, depends on the penetration required and the particular photosensitivity. Light penetration in turn increases with increasing wavelength. One example of a wavelength suitable for the methods described herein is approximately 500 nanometers, although other wavelengths may be equally well suited.

Figure 5:
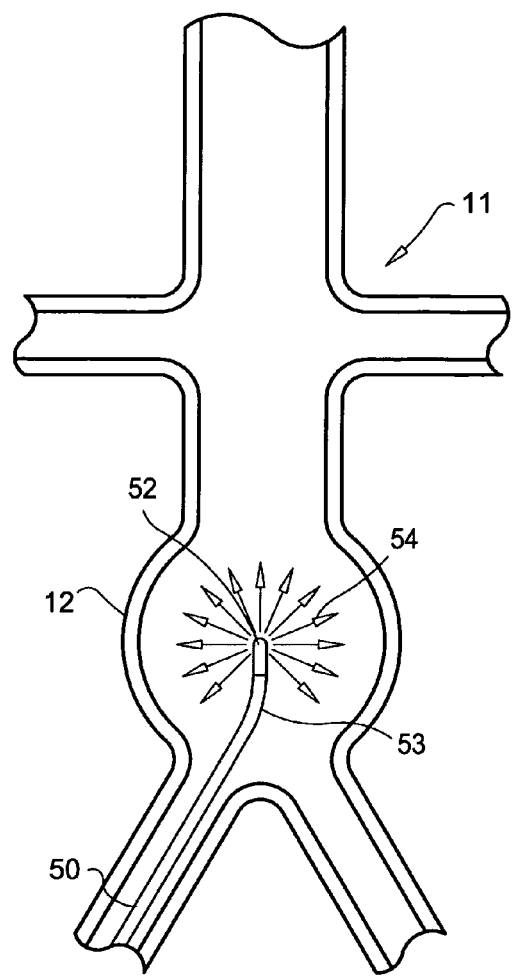
FIG. 5 is a view of a catheter device using laser energy disposed inside of a blood vessel proximate an aneurysm.

In accordance with the preceding method, FIG. 5 illustrates the use of a laser light emitting energy source 52 disposed at the distal end portion 53 of a catheter 50 introduced into a blood vessel 11 proximate aneurysm 12. The laser light is emitted in the direction of one of the arrows 54 in FIG. 5, and thus may be used to target a specific localized region of tissue. The laser light emitting energy source 52 may be fitted with beam direction optics (not shown) to focus and steer the emitted beam in any direction around the distal end portion 53 of catheter 50, as shown by the multi-directional arrows 54. Alternatively, the emitted laser light may be optically directed, using prisms or other optical elements, to be emitted in a diffuse, spherical, or other non-linear three-dimensional waveform to impinge on larger areas of the interior of blood vessel 11 proximate aneurysm 12. Thus, the laser light may be used to create both small, localized treatment areas as well as larger, circumferential lesions, as may be required.

Because laser light is easily tuned to a precise frequency, the light emitted 54 by the laser light emitting energy source 52 can be accurately tuned to trigger exactly the desired response in the cells of the blood vessel 11 near the aneurysm 12. As illustrated by FIG. 5, the distal end portion 53 of the catheter 50 may be easily positioned around the interior of the blood vessel 11, such that the emitted laser light 54 is accurately spatially positioned to affect a specific target region of the aneurysm 12.

The entire process may utilize varying laser wavelengths to achieve varying results. Often the treatment desired is purely for biostimulus, involving effects, which have a lesser permanent effect on tissue. Other times the treatment desired is less mild and seeks to ablate tissue. Examples of the particular laser light wavelengths used for biostimulus are approximately 1,000 nanometers, while that used for ablation is in the neighborhood of approximately 1250 nanometers, as may be delivered by a YAG (Yttrium Aluminum Garnet) laser.

Figure 6:
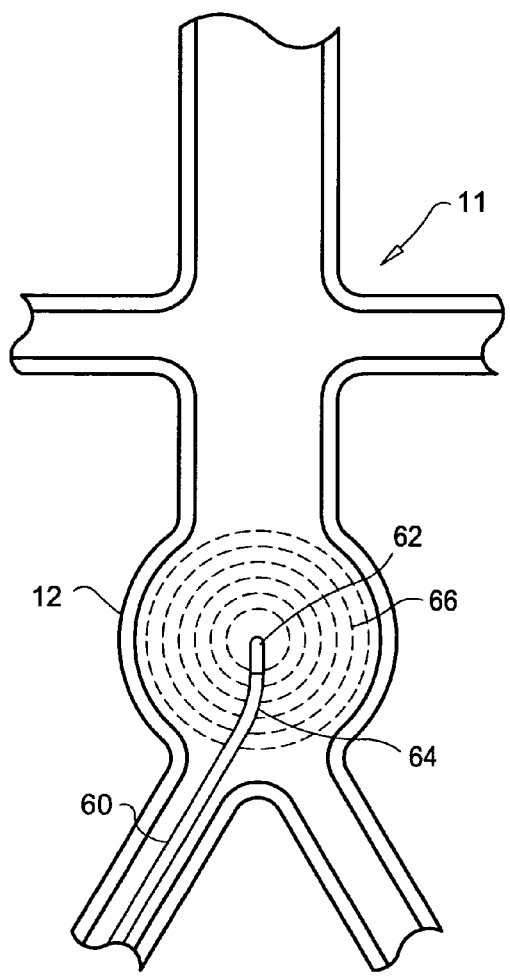
FIG. 6 is a view of a catheter device using sound energy disposed inside of a blood vessel proximate an aneurysm.

FIG. 6 shows an alternative embodiment of the present invention, wherein a catheter 60 is disposed inside of a blood vessel 11 proximate an aneurysm 12, having an energy-emitting element 62 disposed at the distal end portion 64 of said catheter 60. In this embodiment, the energy-emitting element includes a device, which generates periodic mechanical vibrations in the form of sound waves 66. Such sound waves 66 may be anywhere in the sonic, infrasonic, or ultrasonic range, both audible and non-audible. Although generally, ultrasonic energy is preferred to create the desired therapeutic effects on the aneurysm 12. As with the preceding embodiments, the energy emitted by the energy-emitting element 62 propagates though the interior of the blood vessel, through any blood flow, which may be present (not shown) and impinges upon the aneurysm 12. This in turn generates the desired therapeutic reactions in treating the aneurysm 12.

Figure 7:
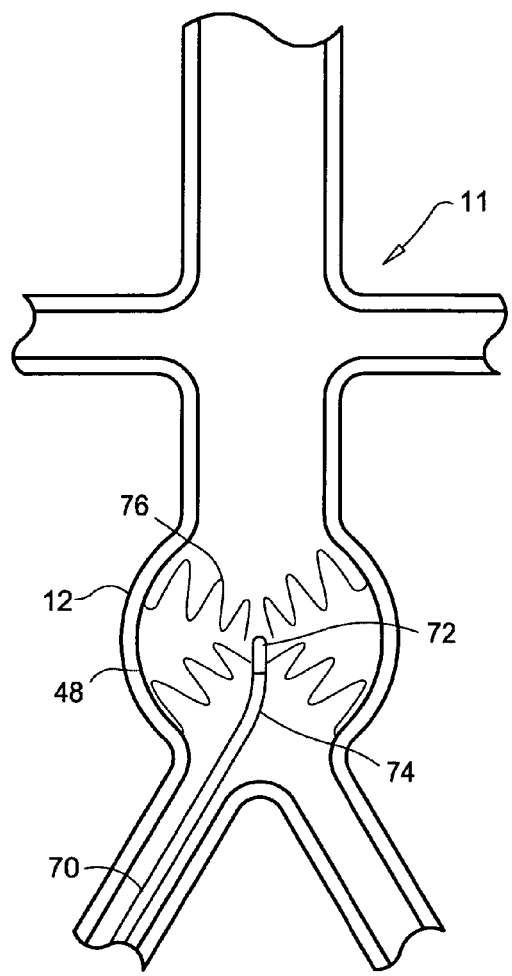
FIG. 7 is a view of a catheter device using microwave energy disposed inside of a blood vessel proximate an aneurysm.

FIG. 7 illustrates still another embodiment of the present invention, wherein a catheter 70 having an energy-emitting element 72 disposed at its distal end portion 74 is introduced into a blood vessel 11 proximate an aneurysm 12. In this embodiment, electromagnetic energy (as labelled by waves 76 in FIG. 7) is emitted from the energy-emitting element 72 to irradiate the inner wall 48 of the blood vessel 11 around the aneurysm 12. The electromagnetic energy may take several forms and frequencies, including both microwave and radiofrequency waves.

Figure 8:
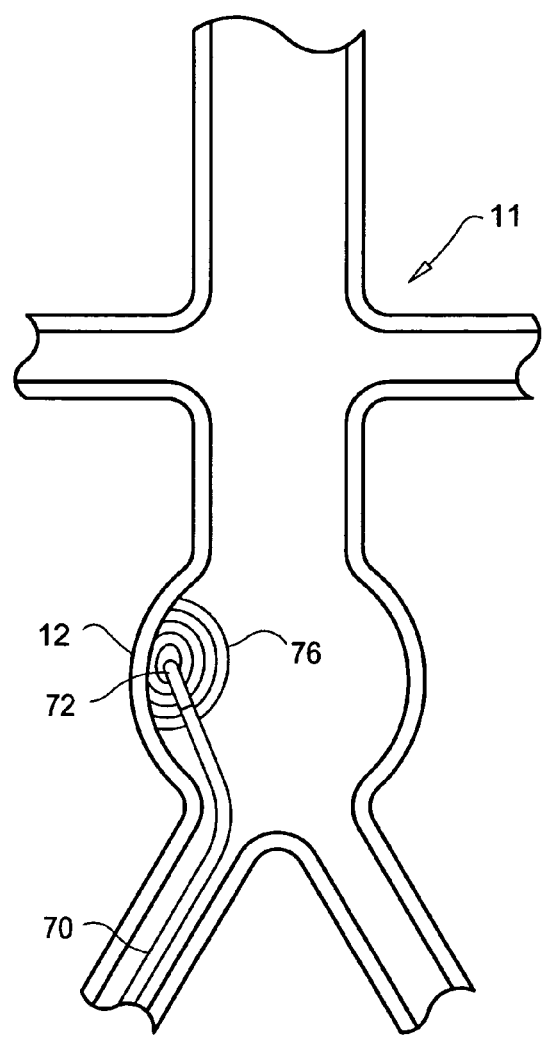
FIG. 8 is a view of a catheter device using radio frequency energy disposed inside of a blood vessel proximate an aneurysm.

All forms of energy as discussed herein trigger some thermal reactions with the blood flow inside the blood vessel 11. In particular, radiofrequency (RF) waves significantly heat up the blood flow. As such, it is desirable to position the catheter 70 as closely as possible to the inner wall 48 of blood vessel 11, as is illustrated in FIG. 8. In this fashion, the energy 76 emitted from the energy-emitting element 72 is better suited to irradiate the aneurysm 12 as desired. The use of microwave, ultrasound or laser light is advantageous over RF energy in that the former three forms of energy are not inhibited by blood flow, and may be readily conducted thereby.

Figure 9:
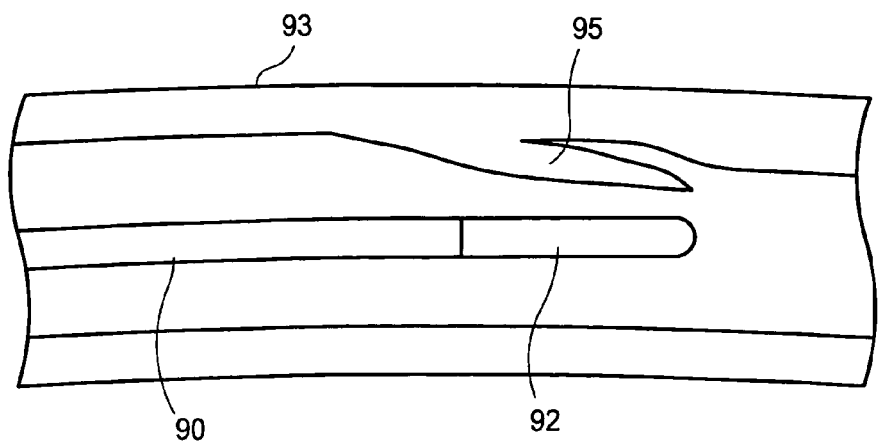
FIG. 9 is a view of a catheter device disposed inside of a blood vessel proximate a dissection.

Additionally, all of the foregoing methods may be equally applied to certain other vascular defects, including vascular dissections as well as aneurysms. FIG. 9 illustrates a catheter device as in the previously shown embodiments disposed inside a vessel proximate a dissection. The catheter 90, having a treatment tip section 92 is positioned inside the vessel 93 proximate a dissection 95. The methods discussed hereinabove are thus applied to treat the tissue, or a tissue region, around and including the lacerated vessel wall of the dissection. The therapeutic effects of the methods disclosed herein apply in much the same manner as with other vascular defects such as aneurysms.

In addition, the foregoing energy-transfer methods involving cryogenic thermal cooling, visible light energy, laser light energy, ultrasound, and microwave and radiofrequency electromagnetic energy may be combined with other treatments for vascular defects, including the use of pharmaceutically active compounds, vaso-occlusive materials, as well as implanted medical devices such as coils, stents, or grafts. Such combined treatments may be delivered to an aneurysm region by a single medical device, or alternatively, through separate medical instruments. Furthermore, the treatments may be applied concurrently, sequentially, or cyclically within a predetermined time period.

Figure 10:
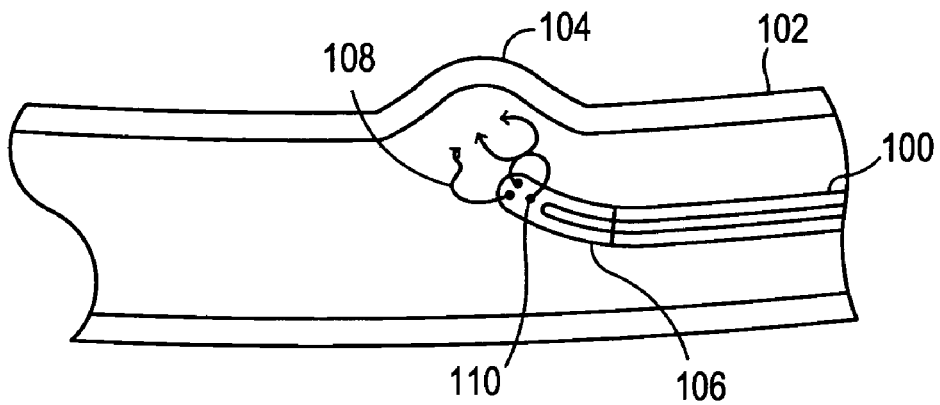
FIG. 10 is a view of a catheter device having an energy-transfer element and delivering a compound inside of a blood vessel proximate an aneurysm.

FIG. 10 shows a step of an alternative method of the present invention, wherein a catheter 100 is disposed inside of a blood vessel 102 proximate an aneurysm 104. The catheter includes an energy-transfer element 106 disposed at the distal end portion and the energy-transfer element may employ any of the above-mentioned energies. In addition to treating the aneurysm tissue region through energy-transfer, the method further may include the dispersion of a vaso-occlusive or pharmaceutically active compound 108 within a close proximity of the aneurysm or vascular defect, such as through a series of apertures 110 in the catheter. A vaso-occlusive compound may include injectable fluids or suspensions, such as microfibrillar collagen, thrombogenic fluids, or polymeric compositions. After such introduction to a tissue site, the vaso-occlusive compounds form a substantially solid space-filling mass, which provides some relief of vessel wall pressure in the region of an aneurysm. Such agents are often introduced into the vasculature through a catheter and are known in the art. Alternatively, a pharmaceutically or biologically active compound may be introduced through the catheter to the region of the aneurysm, including, but not limited to anti-proliferative agents, anti-inflammatory agents, anti-mitotic agents, or anaesthetic agents.

Figure 11:
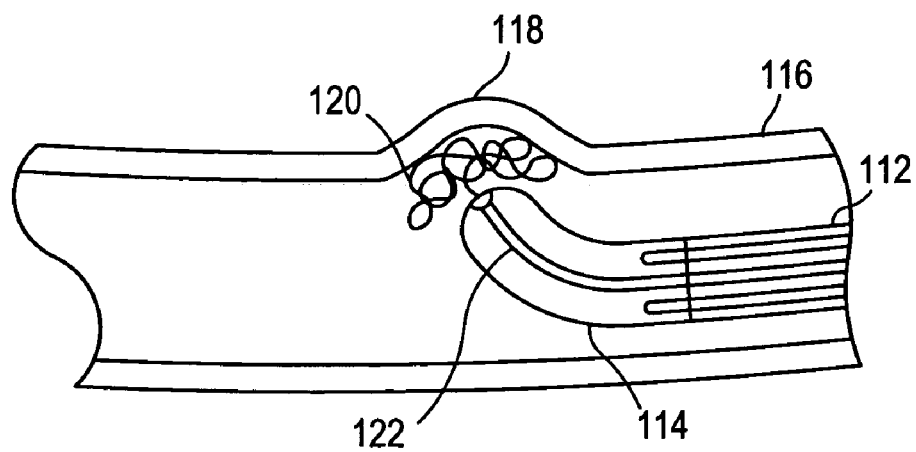
FIG. 11 is a view of a catheter device having an energy-transfer element and delivering a mechanical intravascular device inside of a blood vessel proximate an aneurysm.

FIG. 11 illustrates a step of still another alternative method of the present invention, wherein a catheter 112 having an energy-transfer element 114 disposed at its distal end portion is introduced into a blood vessel 116 proximate an aneurysm 118, where energy-transfer treatment may be provided in addition to the delivery of a mechanical intravascular device 120. The mechanical device 120 may be delivered through a designated lumen 122 within the energy-transfer catheter, or through an additional medical device. A typical mechanical intravascular device is a wire coil or braid, which can be introduced through a catheter in a stretched linear form, which then assumes an irregular shape upon discharge of the device from the end of the catheter. The detached coil is intended to block or impede the flow path of blood into the aneurysm, resulting in the blood being forced past the defect. Moreover, implanted coils may enhance the formation of a clot within the aneurysm, thereby aiding in the prevention of rupture and providing for the eventual sealing of the aneurysm. In addition, the mechanical intravascular device 120 may be coated with a pharmaceutically-active agent, providing a synergistic effect through both mechanically impeding flow into the aneurysm as well as providing drug therapy to the tissue region. By applying an energy-transfer treatment, the collagen content of the surrounding vessel may be increased, thereby enhancing tissue in-growth of the coil to reduce the probability of recanalization to the aneurysm.

Figure 12:
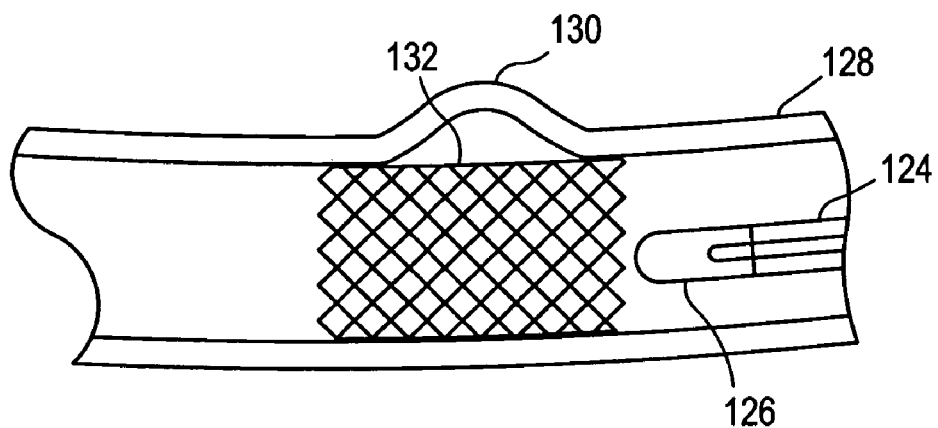
FIG. 12 is a view of a catheter device having an energy-transfer element and delivering an endovascular graft inside of a blood vessel proximate an aneurysm.

Now referring to FIG. 12, a step of yet another method of the present invention provides a catheter 124 having an energy-transfer element 126 disposed at its distal end portion being introduced into a blood vessel 128 proximate an aneurysm 130 in addition to the placement of an endovascular graft 132 at the aneurysm tissue site. Endovascular grafts commonly include a tubular collapsible mechanical framework that can be delivered by catheter to the aneurysm site. Moreover, the graft 132 may also have barb-like anchors that fasten the graft to the walls of the vessel. The endovascular graft 132 is intended to exclude blood flow from reaching the aneurysm while reinforcing the surrounding wall of the vessel, and such endovascular grafts are known in the art. By applying an energy-transfer treatment, the collagen content of the surrounding vessel may be increased, thereby enhancing the attachment of the vascular graft. Moreover, the energy-transfer treatment may be applied to side branch vasculature to induce stenosis and mitigate backflow into the aneurysm, further enhancing the ability of an implanted graft to seal the aneurysm and isolate the defect from blood flow.

Figure 13:
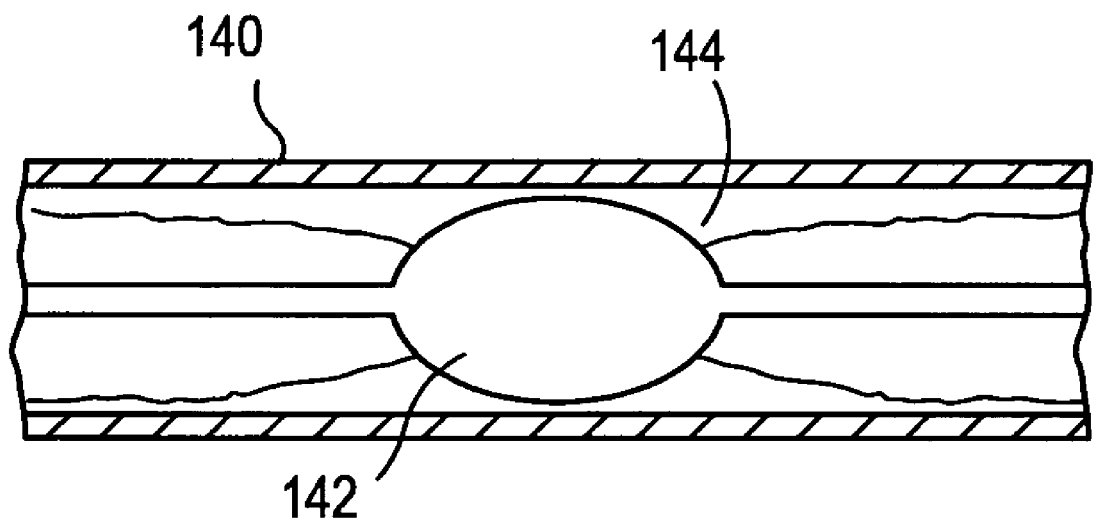
FIG. 13 is a view of a balloon catheter device inflated within a blood vessel to contact an area of vulnerable plaque.

An alternate embodiment, as shown in FIG. 13, a vessel region 140 treated with a balloon catheter 142 and the balloon catheter 142 is infused with a cryogenic fluid and maintained in contact with tissue for a period of time as described above with respect to the cryotreatment of an aneurysm. A balloon catheter is useful in situations where occlusion reduction is necessary and/or where a large area is being treated. In the latter case, the large contact area provided between the outer balloon surface and the vascular wall inner surface makes thermal energy transfer more efficient. In another exemplary procedure, a balloon dilated region of a vessel is cooled prior to implantation of a vascular stent.

As stated above, the combination of the energy-transfer treatment with the additional treatment methods may be applied to a tissue region at substantially the same time through a single medical device. Alternatively, the treatment combinations may be applied sequentially, that is to say, one treatment followed by another treatment shortly thereafter, i.e., in a single medical procedure.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for treating an arterio-venous malformation, comprising:
   providing a catheter having an energy-transfer element;
   positioning said catheter and disposing said energy-transfer element proximate a target tissue region including the arterio-venous malformation,
   treating the target tissue region by transferring thermal energy to the target tissue region, wherein transferring thermal energy comprises at least one of emitting laser light energy, emitting ultrasonic periodic mechanical vibrational energy, emitting microwave electromagnetic energy, and emitting radiofrequency electromagnetic energy;

providing a second treatment proximate a target tissue region including the vascular defect, wherein the step of providing a second treatment includes delivering a biologically active compound to the target tissue region and is performed substantially simultaneously with the step of transferring thermal energy.

2. The method of claim 1, wherein the catheter comprises proximal and distal end portions, said energy-transfer element being disposed on the distal end portion of said catheter.

3. The method of claim 1, wherein method further includes delivering a mechanical intravascular device to the target tissue region.

4. The method of claim 1, wherein the method further includes injecting coolant into an expansion chamber.

5. A method for treating an arterio-venous malformation, comprising the steps of:
providing a catheter having at least one of a laser light energy transfer element, an ultrasonic energy transfer element, a microwave energy transfer element, and a radiofrequency energy transfer element;
positioning said catheter and disposing said energy transfer element proximate a target tissue region including the arterio-venous malformation,
treating the target tissue region by transferring heat energy between the energy transfer element and the target tissue region; and
providing a second treatment proximate a target tissue region including the vascular defect, wherein the step of providing a second treatment includes delivering a biologically active compound to the target tissue region and is performed substantially simultaneously with the step of transferring heat energy; and the biologically active compound is a pharmaceutically-active compound.

6. A method for treating a vascular defect, comprising the steps of:
providing a catheter having at least one of a laser light energy transfer element, an ultrasonic energy transfer element, a microwave energy transfer element, and a radiofrequency energy transfer element;
positioning said catheter and disposing said energy-transfer element proximate a target tissue region including the vascular defect,
treating the target tissue region by transferring heat energy between the energy transfer element and the target tissue region; and
providing a second treatment proximate a target tissue region including the vascular defect, wherein the step of providing a second treatment includes delivering a biologically active compound to the target tissue region and is performed substantially simultaneously with the step of transferring heat energy; wherein the biologically active compound is a vaso-occlusive compound.

7. A method for treating a vascular defect, comprising the steps of:
providing a catheter having an energy-transfer element and an expansion chamber;
positioning said catheter and disposing said energy-transfer element proximate a target tissue region including the vascular defect,
transferring heat energy between the expansion chamber and the target tissue region; and providing a second treatment proximate a target tissue region including the vascular defect, wherein the step of providing a second treatment includes delivering a biologically active compound to the target tissue region and is performed substantially simultaneously with the step of transferring heat energy; and delivering a wire coil to the target tissue region.

8. A method for treating a vascular defect, comprising the steps of:
providing a catheter having an energy-transfer element and an expansion chamber;
positioning said catheter and disposing said energy-transfer element proximate a target tissue region including the vascular defect,
transferring heat energy between the expansion chamber and the target tissue region; and providing a second treatment proximate a target tissue region including the vascular defect, wherein the step of providing a second treatment includes delivering a biologically active compound to the target tissue region and is performed substantially simultaneously with the step of transferring heat energy; and
delivering a wire braid to the target tissue region.

9. A method for treating a vascular defect, comprising the steps of:
providing a catheter having an energy-transfer element and an expansion chamber;
positioning said catheter and disposing said energy-transfer element proximate a target tissue region including the vascular defect,
transferring heat energy between the expansion chamber and the target tissue region; and providing a second treatment proximate a target tissue region including the vascular defect, wherein the step of providing a second treatment includes delivering a biologically active compound to the target tissue region and is performed substantially simultaneously with the step of transferring heat energy; and
delivering an intravascular stent to the target tissue region.

10. A method for treating a vascular defect, comprising the steps of:
providing a catheter having an energy-transfer element and an expansion chamber;
positioning said catheter and disposing said energy-transfer element proximate a target tissue region including the vascular defect,
transferring heat energy between the expansion chamber and the target tissue region; and providing a second treatment proximate a target tissue region including the vascular defect, wherein the step of providing a second treatment includes delivering a biologically active compound to the target tissue region and is performed substantially simultaneously with the step of transferring heat energy; and wherein the vascular defect is a dissection.

* * * * *

UNITED STATES PATENT AND TRADEMARK OFFICE
CERTIFICATE OF CORRECTION

PATENT NO.           : 7,912,554 B2                                                    Page 1 of 1
APPLICATION NO.      : 11/119368
DATED                : March 22, 2011
INVENTOR(S)          : Leonilda Capuano et al.

It is certified that error appears in the above-identified patent and that said Letters Patent is hereby corrected as shown below:

In Column 11, Line 2, change "vascular defect" to --arterio-venous malformation--.
    In Column 11, Line 28, change "vascular defect" to --arterio-venous malformation--.

Signed and Sealed this
Sixteenth Day of August, 2011

David J. Kappos
*Director of the United States Patent and Trademark Office*